United States Patent [19]

El-Gammal

[11] 4,019,382
[45] Apr. 26, 1977

[54] APPARATUS FOR USE IN THE MEASUREMENT OF THE FLOW RATE OF FLUID FLOW

[75] Inventor: Hussein Mokhtar El-Gammal, Hatfield, England

[73] Assignee: Ferraris Development and Engineering Company Limited, London, England

[22] Filed: Mar. 24, 1975

[21] Appl. No.: 561,378

[30] Foreign Application Priority Data

Mar. 25, 1974 United Kingdom .............. 13076/74

[52] U.S. Cl. ........................... 73/194 R; 73/205 R; 128/2.08
[51] Int. Cl.² ......................................... G01F 1/34
[58] Field of Search ............ 73/194 R, 205 R, 515; 128/2.08

[56] References Cited

UNITED STATES PATENTS

| | | | |
|---|---|---|---|
| 3,310,985 | 3/1967 | Bedsterling et al. .................. | 73/515 |
| 3,343,413 | 9/1967 | South et al. ......................... | 73/194 |
| 3,592,042 | 6/1971 | Martinez ............................. | 73/194 X |
| 3,686,937 | 8/1972 | Torey .................................. | 73/194 |
| 3,690,171 | 9/1972 | Tippetts et al. ..................... | 73/194 |
| 3,705,534 | 12/1972 | Tureit ................................ | 73/194 X |
| 3,709,213 | 1/1973 | Yard .................................... | 73/194 |
| 3,803,911 | 9/1972 | Shkatov et al. ...................... | 73/194 |
| 3,876,009 | 4/1975 | Johnson, Jr. ......................... | 73/212 |

OTHER PUBLICATIONS

"Fluidic Wind Sensor Aids Low Airspeed Measurement", in Cont. Eng. vol. 18, No. 4, 4/71, p. 41.

Primary Examiner—Herbert Goldstein
Attorney, Agent, or Firm—Edwin E. Greigg

[57] ABSTRACT

A fluidic flowmeter for measuring the respiratory function of infants or children comprises a duct through which the infant or child breathes. A convergent pair of supply passages are provided for directing a pair of jets across the duct towards a pair of receiver passages which communicate with and diverge from the duct, the jets merging part way across the duct. A pressure tapping is provided in each receiver passage for sensing the static pressure of fluid flow at a respective point in each receiver passage and there is a differential pressure sensitive transducer having an input connected to one end of the pressure tappings and another input connected to the other pressure tapping. In a preferred embodiment the two receiver passages are connected together to define a loop, the dimensions and configuration of that part of the loop with which the tappings communicate being such that the flow passed each tapping is laminar. A temperature sensitive electrical resistance element or a hot-wire anemometer element may be used in place of the pressure tappings to provide a signal which is indicative of non-turbulent fluid flow through the receiver passages if the receiver passages are sized and configured to ensure laminar flow therethrough.

8 Claims, 7 Drawing Figures

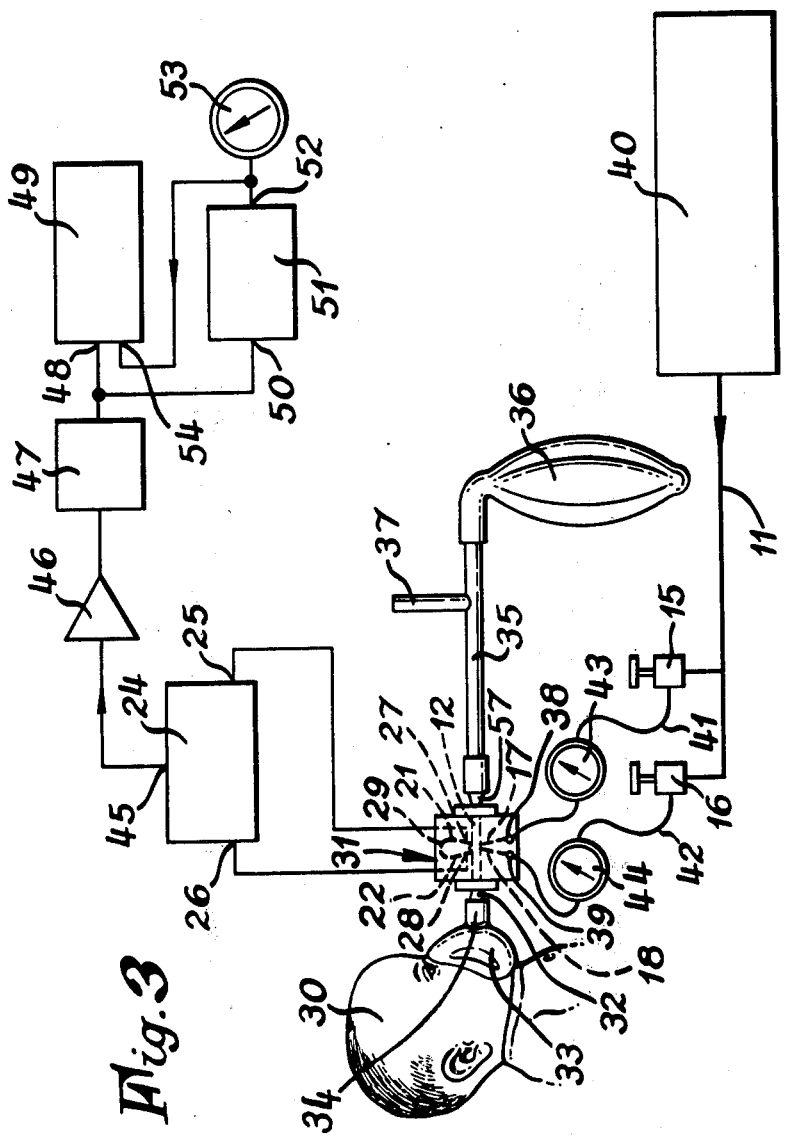

APPARATUS FOR USE IN THE MEASUREMENT OF THE FLOW RATE OF FLUID FLOW

This invention relates to apparatus for use in the measurement of the flow rate of fluid flow, especially apparatus for measuring the flow rate of a pulsating fluid flow through a duct such as respiratory flowmeters which are intended for the measurement of the respiratory function of infants or children.

One form of apparatus which has been proposed for measuring the respiratory function of infants or children comprises a flowmeter which includes pressure fluid supply means for directing at least one jet of fluid under pressure across a duct towards a pair of receiver passages which are arranged symmetrically with respect to the pressure fluid supply means and which each have a mouth which is defined within the wall of the duct, and a differential pressure sensitive transducer which is connected between the two receiver passages and which is operable to generate an output signal which is indicative of the sense and magnitude of any difference between the fluid pressure in the two receiver passages, the arrangement being such that the output signal from the transducer is a measure of the magnitude and direction of fluid flow through the duct.

Measurement of a transient fluid flow condition, such as a pulsating fluid flow, by such apparatus is liable to be complicated by random variations in pressure which lead to the resultant output signal consisting of a signal component which is indicative of the fluid flow that is to be measured and signal components derived from such random variations in pressure. The latter signal components are referred to usually as noise. Conveniently, the output signal is electrical and is fed to a suitable electrically operable indicator. Up to now those who have sought to minimise the incidence of noise signal components in the output signal received by the indicator have provided suitable electrical noise filter circuitry between the transducer and the indicator for the removal of such components from the output signal.

An object of this invention is to minimise or eliminate from the output signal emitted by the transducer signal components which are derived from random variations in pressure.

Broadly, in accordance with this invention, the rate of flow of fluid through a duct of apparatus of the kind referred to is measured by sensing a component of fluid flow within the receiver passages which contains virtually no signal components which are derived from random variations in the total pressure in the receiver passages and deriving from the fluid flow components so sensed a signal, which is representative of fluid flow within the two receiver passages.

According to this invention there is provided apparatus for use in the measurement of the flow rate of a fluid flow, the apparatus comprising a duct through which the fluid flow to be measured is directed, pressure fluid supply means for directing at least one jet of fluid under pressure across the duct towards a pair of receiver passages which each communicate with the duct, and means which are associated with a non-turbulent component of fluid flow within each receiver passage for the derivation of at least one signal which is indicative of the associated non-turbulent component of fluid flow, the arrangement being such that an indication of the flow rate of fluid flow through the duct can be derived from the signal or signals.

Preferably said means which are associated with a non-turbulent component of fluid flow within each receiver passage comprise a pressure tapping for sensing the static pressure of fluid flow at a respective point in each receiver passage so that the signal that is derived by each said means is a static fluid pressure signal. The apparatus may include or be designed for use with a differential pressure sensitive transducer having a pair of fluid pressure input ports, each pressure tapping being in communication with a respective one of the input ports.

The pair of receiver passages may be arranged symmetrically with respect to the pressure fluid supply means. Each receiver passage has a mouth which is defined within a wall of the duct and may include an arcuate recess within the wall of the duct between the mouths of the receiver passages.

Each receiver passage has a mouth which is defined within a wall of the duct and the two receiver passages may be connected together so as to define a loop by which the said mouths communicate one with the other, the dimensions and configuration of the part of parts of the loop with which said means which are associated with a non-turbulent component of fluid flow within each receiver passage communicate being such as to ensure that fluid flow therewithin is laminar. The said means which are associated with a non-turbulent component of fluid flow within each receiver passage may comprise a temperature sensitive electrical resistance element which is supported within such a part of the loop that is designed to ensure that fluid flow therewithin is laminar.

According to another aspect of this invention there is provided apparatus for use in conjunction with a differential pressure sensitive transducer to measure the flow rate of a fluid flow, the apparatus comprising a duct through which the fluid flow to be measured is directed and pressure fluid supply means for directing at least one jet of fluid under pressure across the duct towards a pair of receiver passages which are arranged symmetrically with respect to the pressure fluid supply means and which each have a mouth which is defined within a wall of the duct, each receiver passage having a pressure fluid tapping, the pair of pressure fluid tappings being arranged for connection to respective inlet ports of the differential pressure sensitive transducer when the apparatus is in use, wherein said pressure fluid tappings are arranged so that the fluid pressure signal which each transmits to the respective inlet port of the differential pressure transducer when the apparatus is in use is a static fluid pressure signal which is representative of the static pressure of fluid flow at the respective point in the respective receiver passage.

A flow restricting device may be connected between the two receiver passages. Also apparatus for removing random variations in pressure from the fluid pressure signal that is transmitted from each receiver passage to the respective fluid pressure tapping may be provided.

Each pressure fluid tapping may be at a point in the respective receiver passage which is as close as is practicable to the said mouth of that receiver passage.

Where the two receiver passages are connected together so as to define a loop by which the said mouths communicate one with the other, the dimensions and configuration of that part of the loop between those points at which the static fluid pressure signals are derived preferably is such as to ensure that fluid flow therewithin is laminar.

The pressure fluid supply means may comprise a pair of pressure fluid supply passages for directing a pair of jets of fluid under pressure across the duct towards the receiver passages, the axes of the two supply passages being convergent so that jets directed by the supply passages towards the receiver passages meet part way across the duct. In a preferred form of apparatus according to this invention, the angle included between the two supply passages is an acute angle and is selected so as to avoid an unacceptable loss of energy from the flow of fluid through the supply passages which results in the jets being formed. Reducing the angle included between the fluid pressure supply passages may render the resultant apparatus more sensitive.

The pair of pressure fluid supply passages may be connected to a common source of fluid pressure through a fluidic differential amplifier, the pressure tapping of each of the pair of receiver passages being connected to a respective one of an opposed pair of pressure inputs of the amplifier.

Conveniently the pressure fluid supply means comprise a single pressure fluid supply passage, suction means having a suction inlet which is in communication with the duct and an outlet which is in communication with the single pressure fluid supply passage, the arrangement being such that, in use of the apparatus, the suction means operate to suck fluid from the duct and to feed it to the single pressure fluid supply passage for direction therethrough and across the duct towards the pair of receiver passages. The suction inlet may be connected to the duct between the pair of receiver passages and opposite the single pressure fluid supply passage. The suction means may comprise a suction pump.

Various embodiments of apparatus according to this invention will be described now by way of example with reference to the accompanying drawings, of which:

FIG. 3 is a circuit diagram of apparatus with which the flowmeter shown in FIG. 2 is used in practice;

Figure 1:
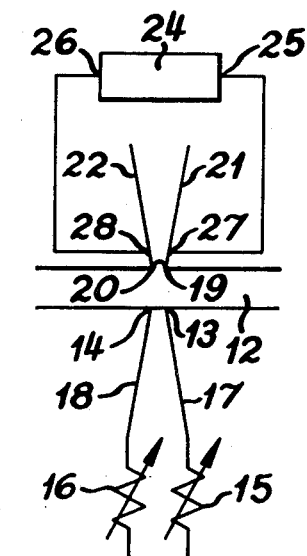
FIG. 1 is a diagram illustrating one form of flowmeter for measuring the respiratory function of infants or children which includes apparatus according to this invention.

The flowmeter shown diagrammatically in FIG. 1 has an input tapping 11 for connection to a source of compressed air, such as a constant pressure air pump or a source of an anaesthetic or resuscitatory gas mixture and a duct 12 through which the infant or child breathes.

The input tapping 11 is connected to each of two axially spaced ports 13 and 14 in the wall of the duct 12 through a respective adjustable pressure control device 15, 16 and a respective supply passage 17, 18. The supply passges 17 and 18 terminate in the ports 13 and 14 respectively and their axes converge towards a notional point within the duct 12 and include an acute angle between them, the notional point lying within a notional plane which bisects the acute angle that is included between the two supply passages 17 and 18.

Another pair of ports 19 and 20 are defined in the wall of the duct, the port 19 being opposite the port 13 and the port 20 being opposite the port 14. The port 19 is the mouth of one receiver passage 21 and the port 20 is the mouth of another receiver passage 22. The axes of the two receiver passages 21 and 22 also converge towards a notional point which is within the notional plane that bisects the acute angle that is included between the two supply passages 17 and 18. The receiver passages 21 and 22 are closed at their ends remote from the mouths 19 and 20. The axes of the supply passages 17 and 18, the receiver passages 19 and 20 and the duct 12 all lie in a common plane.

A differential pressure sensitive transducer 24 is connected between a pair of output tappings 25 and 26 of the flowmeter. The output tapping 25 is connected to a pressure tapping 27 in the receiver passage 21, the pressure tapping 27 being an orifice in the inner surface of the receiver passage 21 and being as close to the mouth 19 thereof as is practicable. The output tapping 26 is connected to another pressure tapping 28 in the receiver passage 22, the pressure tapping 28 being an orifice in the inner surface of the receiver passage 22 and being as close to the mouth 20 thereof as is practicable. Hence a fluid pressure signal is transmitted from each pressure tapping 27, 28 via the respective output tapping 25, 26 to the respective input of the transducer 24, the fluid pressure signals so transmitted being representative of the static head component of fluid pressure in the respective receiver passage 21, 22. The transducer 24 may incorporate an indicating device for presenting an output signal which is indicative of a difference between the static head components of pressure within the two receiver passages 21 and 22 and thus of a pressure differential between those two passages 21 and 22, or may be connected to a separate device for presenting such a signal. The indicator may be an oscilloscope, a pen and moving chart recorder, a voltmeter or any other suitable form of indicating device. The detailed construction and manner of operation of the transducer 24 is not described herein. It is sufficient to know that any form of diffferential pressure sensitive transducer, such as a Greer Micromanometer which is obtainable from Mercury Electronics (Scotland) Limited, Glasgow, Scotland, which will respond to a difference between the pressure at the output tapping 25 and the pressure at the output tapping 26 in order to produce a signal which is indicative of such a pressure difference can be used as the transducer 24.

When the apparatus is set up for use to measure the respiratory function of a child or infant, the tapping 11 is connected to the source of compressed air, anaesthetic or resuscitatory gas. Such air or gas is fed under pressure through the tapping 11. Either or both adjustable pressure controllers 15 and 16 are set so that the pressure of the two jets of air or gas which emerge from the ports 13 and 14 is the same. Thus, under conditions of no axial flow through the duct 12, the two jets impinge part way across the duct 12 and merge into a single radially directed jet which strikes the wall of the duct 12 midway between the two receiver ports 19 and 20 so that the pressure at the receiver port 19 is substantially equal to that at the receiver port 20. If it is found that the indicator presents a reading which is other than zero under conditions of no axial flow through the duct 12, the indicator is balanced to indicate zero by adjustment of suitable adjustment means provided. The air or gas from which the jets are composed is exhausted to atmosphere through the duct 12 in the direction away from the end of the duct that is connected to a mouthpiece for a subject child or infant.

Once the flowmeter has been set up for use, the end of the duct 12 that is connected to the mouthpiece is placed in communication with the nose and mouth of the subject child or infant so that a pulsating axial flow is established within the duct 12 by the child or infant as it breathes. Such an axial flow interacts with the jets of air or gas which are directed across the duct 12 from the supply passages 17 and 18 so as to change the pressure conditions which exist at the ports 19 and 20. The degree of pressure change at any one instant is related substantially linearly to the instantaneous rate of fluid flow by which it was caused so that the consequent pressure differential, which is sensed by the flow transducer 24 and which is indicated by the related indicating device, is an indication of the instantaneous rate of inhalation and exhalation of the subject child or infant.

Use of pressure tappings which sense static head components of fluid pressure results in the fluid pressure signals transmitted to the transducer 24 being derived from velocity independent components of fluid flow through the receiver passages so that the static fluid pressure signals so transmitted contain virtually no signal components which are derived from random variations in the total pressure in the receiver passages 21 and 22.

The continuous flow of air or gas from the supply passages 17 and 18 into the duct 12 and then to atmosphere through the duct 12 minimises the establishment of pockets of static air or gas within the duct 12 and flushes from the duct 12 any matter which may be introduced into the duct 12 by or from a subject child or infant with consequent benefits from the viewpoint of safety and hygiene.

A fixed flow restricting device, which functions as a damping restriction, may be connected between the two receiver passages 21 and 22, each tapping 27, 28 being between the port 19, 20 of the respective receiver passage 21, 22 and the connection to the fixed flow restricting device. A fixed flow restricting device may be connected between the pressure fluid tapping 25 and the respective tapping 27. Another fixed flow restricting device may be connected between the pressure fluid tapping 26 and the respective tapping 28. Such two flow restricting would be selected so that the transducer 24 is connected symmetrically within the fluid circuit as regards the flow restricting characteristics of the various components of the circuit are concerned. The fluid circuit may include apparatus for removing random variations in pressure from the fluid pressure signal that is transmitted from each receiver passage 21, 22 to the respective fluid pressure tapping if desired.

Figure 2:
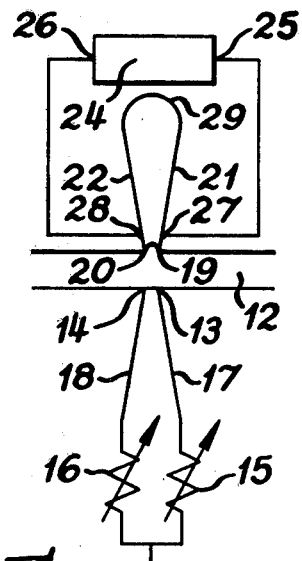
FIG. 2 is a diagram, similar to FIG. 1, illustrating another form of flowmeter for the same purpose.

The flowmeter shown diagrammatically in FIG. 2 is similar in most respects to that shown in FIG. 1 and only those parts which differ will be described now. Parts of the flowmeter shown in FIG. 2 which are similar to that described above with reference to FIG. 1 have been given the reference numeral which was used to identify the corresponding part in FIG. 1.

The receiver passages 21 and 22 are connected together by a curved passage 29 so that they co-operate with that curved passage 29 to define a loop by which each of the mouths 19 and 20 communicates with the other. The length and configuration of that part of the loop which extends between the pressure tappings 27 and 28 is such as to ensure laminar flow of fluid between tappings 27 and 28. The criteria necessary to ensure such laminar flow are well known and will not be explained herein. The fluid pressure signals that are transmitted from the tappings 27 and 28 to the respective inputs 25 and 26 of the differential pressure sensitive transducer 24 are derived from the velocity independent pressure components of the laminar flow passed the tappings 27 and 28. The tappings 27 and 28 are spaced sufficiently from the mouths 19 and 20 so that they are not subjected to turbulent flow conditions which may prevail at the mouths 19 and 20.

Selection of a passage which ensures laminar flow between the tappings 27 and 28 ensures that the fluid pressure signals transmitted to the transducer 24 are derived from velocity independent components of the laminar flow through the receiver passages 21 and 22.

FIG. 3 shows diagrammatically apparatus which has been used in an operating theatre in order to monitor the respiratory performance of a 5 month old male infant whose head is shown at 30. The duct 12, supply passages 17 and 18, receiver passages 21 and 22 and the connecting curved passage 29 are formed in a block 31.

One end of the duct 12 terminates in a fitting 32 which supports a face mask 33 for the infant. The face mask 33 surrounds the nose and mouth of the head 30 and places the duct 12 in communication with the space that is defined between the face mask 33 and the face of the infant through a short coupling 34 which is part of the face mask 33. The other end of the duct 12 is connected to another fitting 35 which carries the usual reservoir bag 36. The fitting 35 defines a conduit, which places the interior of the reservoir bag 36 in communication with the duct 12, and a vent pipe 37 which vents that conduit to atmosphere. The block 31 has tappings 38 and 39 for connecting the supply passages 17 and 18 to external pipes, as well as the tappings 27 and 28.

The output of a conventional anaesthetic machine 40 is connected to the tapping 11. Each pressure control device 15, 16 is connected by a suitable pipe 41, 42 to the respective tappings 38, 39 via a respective pressure gauge 43, 44.

The output 45 from the differential pressure sensitive transducer 24 is connected to an input of an amplifier 46. The output of the amplifier 46 is connected through a selector switch 47 to one input 48 of a chart recorder 49 and to an input 50 of an integrator circuit 51. The output 52 of the integrator circuit 51 is connected to a voltmeter 53 and to another input 54 of the chart recorder 49. The chart recorder 49 gives a continuous readout of the rate of flow of air inhaled and exhaled by the infant under observation. There is also the capability of extracting from the chart recorder 49 an indication of the total volume of air inhaled or exhaled by the infant over a given time period. The voltmeter 53 indicates the volume of air inhaled and/or exhaled by the infant, either breath by breath, or over a given time period, in terms of volts.

Figure 4:
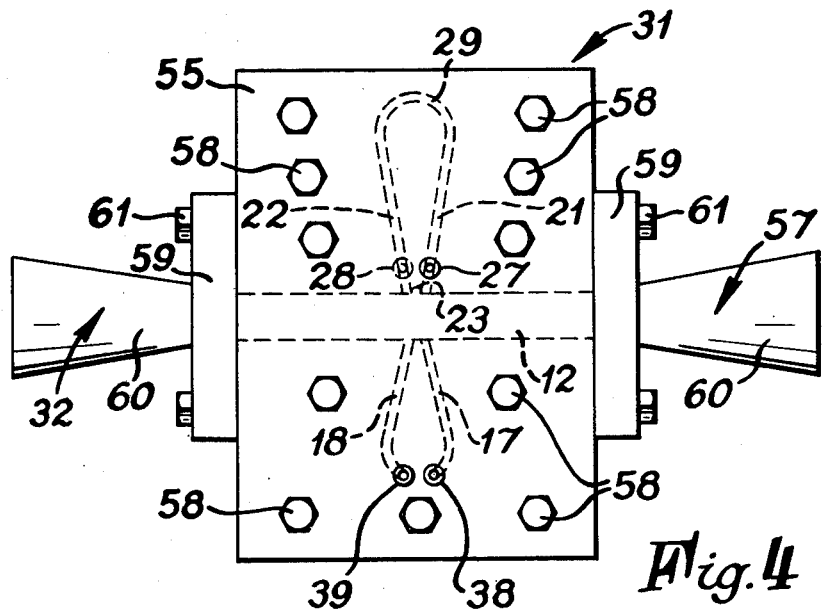
FIG. 4 is a side elevation of a practical embodiment of part of the flowmeter illustrated in FIG. 3.
Figure 5:
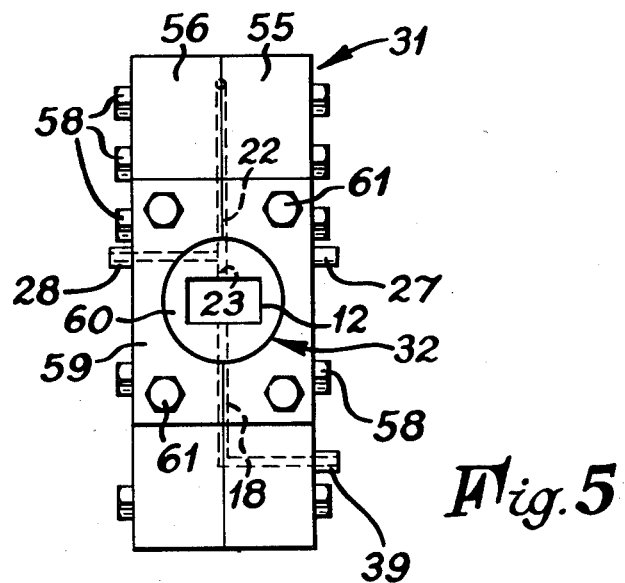
FIG. 5 is an end elevation of the flowmeter part shown in FIG. 4.

FIGS. 4 and 5 show the detailed construction of the block 31 which comprises two rectangular plates 55 and 56 of rigid plastics material, the fitting 32 and a transition piece 57 which is similar to the fitting 32 and is for connecting the duct 12 to the fitting 35.

Conveniently the two mating faces of the plates 55 and 56 are grooved to define the duct 12 which has a rectangular cross-section, the supply passages 17 and 18, the receiver passages 21 and 22 and the connecting loop passage 29. The passages 17, 18, 21, 22 and 29 defined by grooves in the two plates 55 and 56 may have a circular cross-section or a rectangular cross-section. Alternatively the grooves may all be formed in one of the plates 55, 56, the mating face of the other plate 55, 56 being planar and being arranged to close the grooves so that the passages 17, 18, 21, 22 and 29 would have to be rectangular or D-shaped in cross-section. The plates 55 and 56 are held together by securing bolts 58. Conveniently the tapping 27 is carried by one of the plates 55 and 56 and the tapping 28 is carried by the other plate 55, 56 so that the two tappings 27 and 28 emerge on opposite sides of the block 31. This arrangement avoids difficulties that arise because the two orifices in the walls of the passages 21 and 22 at the inner end of the tappings 27 and 28 are closely spaced. The two tappings 27 and 28 could emerge on the same side of the block 31 if they are angled to the planar faces of the plate 55, 56 by which they are carried.

We have found that the performance of the flowmeter is enhanced by the provision of an arcuate recess 23 within the wall of the duct 12 between the mouths 19 and 20 of the receiver passages 21 and 22 and opposite the mouths 13 and 14 of the supply passages 17 and 18, the surface of the arcuate recess comprising part of an internal cylindrical surface which has its axis normal to the notional plane that includes the axes of the two supply passages 17 and 18 and of the two receiver passages 21 and 22. In this construction the axes of the supply passages 17 and 18 meet at a point on the longitudinal axis of the duct 12 and the axes of the receiver passages meet at a point which is on the opposite wall of the duct 12.

Each of the fitting 32 and transition piece 57 is formed of a convenient metal, such as copper, and comprises an apertured rectangular base block 59 and a coaxial tubular part 60. The aperture of the block 59 is central, is rectangular in cross-section, and is aligned with the duct 12. The base block 59 is secured to the respective sides of the two plates 55 and 56 by four setscrews 61. The tubular part 60 has a thin wall and has a varying cross-section which changes progressively from a rectangular cross-section at the end which is connected to the respective base block 59 to a circular cross-section at the other, outer, end.

The flowmeter as described above with reference to either FIG. 1 or FIGS. 2 to 5 can be arranged to indicate the direction, as well as the magnitude, of the fluid flow to be measured. Moreover, the flowmeter has linear characteristics which can be repeated from one instrument to the next within acceptable tolerances. The flowmeter is particularly suitable for measuring the respiratory function of a child or infant because it can function effectively to measure the necessary low flow rates, and also because the pressure drop through the duct 12 does not lead to an unacceptable restriction of the subject child or infant's breathing. In addition it is a simple and inexpensive instrument. Also it has been found that the calibration of the flowmeter is not affected by the humidity of infant or child's breath which varies with changes in the conditions of use.

A flowmeter according to this invention can be used to measure any fluid flow and is not limited to the measurement of pulsating fluid flow. The pair of pressure supply passages 17 and 18 may be replaced by a single pressure fluid supply passage with which the receiver passages 21 and 22 are orientated symmetrically although use of a pair of pressure supply passages is preferred because the location and direction of the single jet which is formed by combination of the pair of jets emitted by such a pair of passages can be controlled readily by adjustment of fluid flow through either or both the supply passages.

Figure 6:
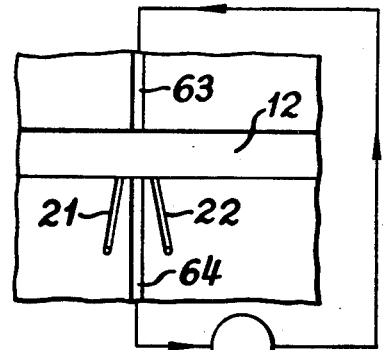
FIG. 6 is a diagram, similar to FIG. 1, illustrating part of another form of flowmeter which embodies apparatus according to this invention.

FIG. 6 shows that the pump 62 which supplies compressed air to the duct 12 through its output and through such a single pressure fluid supply passage 63 can be arranged to draw air through its inlet from the duct 12 via a passage 64 which is located between the two receiver passages 21 and 22 and which is aligned with the single supply passage 63. The pair of receiver passages 21 and 22 may be closed at their ends remote from the mouths 19 and 20, as in the aparatus described above with reference to FIG. 1, or may be connected together to form a loop in a manner similar to the arrangement that has been described above with reference to FIG. 2.

Figure 7:
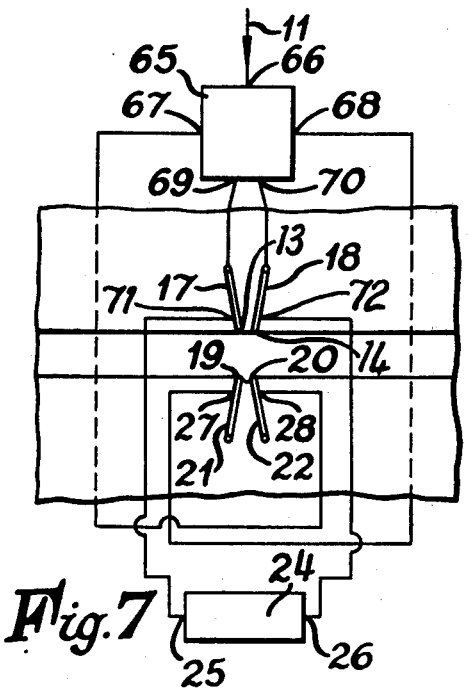
FIG. 7 is a diagram, similar to FIG. 6 illustrating part of yet another form of flowmeter which embodies apparatus according to this invention.

FIG. 7 illustrates a flowmeter which is similar in many respects to that which has been described above with reference to FIG. 1 and only those parts which differ will be described now. Parts of the flowmeter shown in FIG. 7 which are similar to that described above with reference to FIG. 1 have been given the reference numeral which was used to identify the corresponding part in FIG. 1.

A known fluidic differential amplifier device 65 is connected between the input tapping 11 and the pair of supply passages 17 and 18. The pair of pressure control devices 15 and 16 may be omitted but can be included if required to assist initial adjustment in the manner already described. The amplifier 65 has a common supply input 66, opposed pressure inputs 67 and 68 which are on opposite sides of the device 65 and two flow outputs 69 and 70. The output 69 is connected to the supply passage 17. The output 70 is connected to the supply passage 18. The pressure tapping 27 of the receiver passage 21 is connected to the input 68. The pressure tapping 28 of the receiver passage 22 is connected to the input 67. The differential amplifier 65 is such that change of pressure at the input 67 controls the output flow at the flow output 70 while change of pressure at the input 68 controls the output flow at the flow output 69 so that for increase in pressure at an input there is an increase in flow at the corresponding output and for a decrease in pressure at an input there is a decrease in flow at the corresponding output. Each supply passage 17, 18 has a respective pressure tapping 71, 72 which is connected to the respective input of the transducer 24 via the respective output terminal 25, 26.

When the flowmeter is set up for use, the tapping 11 is connected to a source of compressed air and compressed air is fed through that spring 11 to the common supply input 66 of the amplifier device 65. Such compressed air emerges from the two outputs 69 and 70 and is directed through the respective supply passages 17 and 18 to emerge from the mouths 13 and 14 thereof as a pair of convergent jets which merge in the manner already described into a single jet partway across the duct 12. If the single jet does not strike the wall of the duct 12 midway between the mouths 19 and 20 of the two receiver passages 21 and 22 when there is no axial flow through the duct 12, the flow into one of the receiver passages, say the passage 21, will be greater than the flow into the other receiver passage 22. If the flow into the receiver passage 21 is greater than that into the receiver passage 22, the pressure signal at the input 68 will be greater than that at the input 67 so causing a greater proportion of the flow of compressed air which passes through the amplifier device 65 to be directed through the outlet 69 than through the outlet 70. Hence a greater flow will emerge from the mouth 13 than from the mouth 14 so that the single jet is deflected away from the receiver passage 21 and towards the receiver passage 22. Hence the feedback to the respective input 67 or 68 of any change of pressure due to the flow differential between the flows through the receiver passages 21 and 22 leads to a reduction in that flow differential so that the device tends to restore equalisation of flows into the two receiver passages 21 and 22 automatically and is thus operating in the well known class of measuring instruments known as Null-Seeking instruments.

Measurement of the magnitude and direction of any axial flow through the duct 12 by comparison in the transducer 24 of the static pressure head components of fluid flow through the two supply passages 17 and 18 will be apparent from the foregoing description with reference to FIG. 1. The two receiver passages 21 and 22 may be connected together by a curved passage 29 as described above with reference to FIG. 2 if desired, the dimensions and configurations of the connecting loop being such that flow between the two tappings 27 and 28 is laminar.

The various embodiments of the invention which have been described above with reference to FIGS. 1 to 6 of the drawings involve the comparison in the differential pressure sensitive transducer of the static head pressure components of fluid flow through the two receiver passages, the difference between the static head pressure components being a measure of fluid flow through the duct 12. A simple comparison between the fluid flows through the two receiver passages can be used to evolve a useful measure of fluid flow through the duct 12 if the flow through the two receiver passages is laminar and not turbulent. Hence, in each of the embodiments described above which have the two receiver passages interconnected by a passage to define a loop between the mouths of the two receiver passages, the dimensions and configuration of the loop being such as to ensure laminar flow through the loop, the output electromotive force from a hot-wire anemometer element which is suspended within the laminar flow through the loop, or the magnitude of the current that flows in an electrical circuit which includes an electrical resistance element, such as a thermistor, whose electrical resistance varies with the temperature of the element and which is supported within the laminar flow, can be used as a measure of fluid flow through the duct 12. The output electromotive force from such a hot-wire anemometer element would be indicated by a voltmeter which is connected between the two output terminals of the hot-wire anemometer element. The electrical circuit which includes such a temperature sensitive electrical resistance element would also comprise a source of electrical potential and an indicator device, such as an ammeter or a galvanometer, each connected in series with the other and with the resistance element.

I claim:

1. Apparatus for use in the measurement of the flow rate of a fluid flow, the apparatus comprising:
   a body which defines a duct through which the fluid flow to be measured is directed;
   at least one pressure fluid supply passage formed in the body in communication with the duct, adapted for connection to a source of fluid pressure and orientated with respect to the duct so that, in use of the apparatus, it directs a jet of fluid under pressure across the duct;
   a pair of receiver passages formed in the body and in communication with the duct opposite said at least one pressure fluid supply passage, said pair of receiver passages being arranged symmetrically with respect to said at least one pressure fluid supply passage, each receiver passage having a mouth which is defined within a wall of the duct; and
   sensing means for sensing a non-turbulent component of fluid flow within each receiver passage for the derivation of at least one signal which is indicative of the associated non-turbulent component of fluid flow, the arrangement being such that an indication of the flow rate of fluid flow through the duct can be derived from said at least one signal;
   wherein the two receiver passages are connected together so as to define a loop by which said mouths communicate one with the other, the dimensions and configuration of the part of the loop with which said sensing means communicate being such as to ensure that fluid flow therewithin is laminar.

2. Apparatus according to claim 1, further comprising a differential pressure sensitive transducer having a pair of fluid pressure input ports, wherein said sensing means comprise a pressure tapping for sensing the static pressure of fluid flow at a respective point in each receiver passage so that the signal that is derived by each said sensing means is a static fluid pressure signal, and wherein each pressure tapping is in communication with a respective one of the input ports.

3. Apparatus for use in conjunction with a differential pressure sensitive transducer to measure the flow rate of a fluid flow, the apparatus comprising:
   a body which defines a duct through which the fluid flow to be measured is directed;
   at least one pressure fluid supply passage formed in the body and in communication with the duct, said at least one pressure fluid supply passage being adapted for connection to a source of fluid pressure so as to direct at least one jet of fluid under pressure across the duct; and
   a pair of receiver passages formed in the body and in communication with the duct opposite said at least one pressure fluid supply passage with which they are arranged symmetrically through respective mouths which are defined within a wall of the duct, each receiver passage having a pressure fluid tapping, the pair of pressure fluid tappings being arranged for connection to respective inlet ports of the differential pressure sensitive transducer when the apparatus is in use, said pressure fluid tappings being arranged so that the fluid pressure signal which each transmits to the respective inlet port of the differential pressure transducer when the apparatus is in use is a static fluid pressure signal which is representative of the static pressure of fluid flow at the respective point in the respective receiver passage;

wherein the two receiver passages are connected together so as to define a loop by which the mouths communicate one with the other, the dimensions and configuration of that part of the loop between those points at which the static fluid pressure signals are derived being such as to ensure that fluid flow therewithin is laminar.

4. Apparatus according to claim 3, wherein a pair of pressure fluid supply passages for directing a pair of jets of fluid under pressure across the duct towards the receiver passages are formed in the body, the axes of the two supply passges being convergent so that jets directed by the supply passages towards the receiver passages meet part way across the duct.

5. Apparatus according to claim 4, wherein the angle included between the two supply passages is an acute angle.

6. Apparatus according to claim 3, wherein the pressure fluid supply means comprise a single pressure fluid supply passage, suction means having a suction inlet which is in communication with the duct and an outlet which is in communication with the single pressure fluid supply passage, the arrangement being such that, in use of the apparatus, the suction means operate to suck fluid from the duct and to feed it to the single pressure fluid supply passage for direction therethrough and across the duct towards the pair of receiver passages.

7. Apparatus for use in the measurement of the flow rate of a fluid flow, the apparatus comprising:
   a body which defines a duct through which the fluid flow to be measured is directed;
   a pair of pressure fluid supply passages formed in the body in communication with the duct, adapted for connection to a source of fluid pressure and orientated with respect to the duct so that, in use of the apparatus, the pair of supply passages directs a pair of jets of fluid under pressure across the duct, the axes of the two supply passages being convergent so that the jets meet part way across the duct, each supply passage having a pressure fluid tapping for sensing static fluid pressure therein;
   a pair of receiver passages formed in the body and in communication with the duct opposite the two supply passages with which they are arranged symmetrically through respective mouths which are defined within a wall of the duct, each receiver passage having a pressure fluid tapping;
   a fluidic differential amplifier device having
      a common supply input, connecting to a source of pressurized fluid,
      two opposed pressure inputs, each connecting with a respective one of the receiver passage pressure tappings; and
      two flow outputs, each connecting with a respective one of the supply passages, and controlled by the pressure inputs so that any change in the differential pressure between the two pressure inputs produces a change in the flow differential between the two flow outputs tending to equalize the pressures of the two pressure inputs; and
   a differential pressure sensitive transducer having a piar of fluid pressure input ports, each input being in communication with a respective one of the supply pressure tappings for producing a signal proportional to the difference in static pressure between the fluid flow in the two supply passages, said signal being proportional to the flow rate of fluid flow through the duct.

8. Apparatus according to claim 7, wherein the two receiver passages are connected together so as to define a loop by which the mouths communicate one with the other, the dimensions and configuration of that part of the loop between the two receiver passage pressure fluid tappings being such as to ensure laminar fluid flow therewithin.

* * * * *